United States Patent [19]

Kolter et al.

[11] Patent Number: 5,681,588
[45] Date of Patent: Oct. 28, 1997

[54] DELAYED RELEASE MICROTABLET OF β-PHENYLPROPIOPHENONE DERIVATIVES

[75] Inventors: Karl Kolter, Limburgerhof; Helmut Fricke, Mutterstadt; Volker Buehler, Karlsruhe; Herbert Mueller-Peltzer, Heidelberg, all of Germany

[73] Assignee: Knoll Aktiengesellschaft, Ludwigshafen, Germany

[21] Appl. No.: 525,749

[22] PCT Filed: Mar. 24, 1994

[86] PCT No.: PCT/EP94/00949

§ 371 Date: Oct. 3, 1995

§ 102(e) Date: Oct. 3, 1995

[87] PCT Pub. No.: WO94/22434

PCT Pub. Date: Oct. 3, 1994

[30] Foreign Application Priority Data

Apr. 3, 1993 [DE] Germany ............... 43 10 963.2

[51] Int. Cl.$^6$ ................................. A61K 9/20
[52] U.S. Cl. ................. 424/464; 424/469; 424/461; 424/468; 424/458
[58] Field of Search ................. 424/464, 456; 252/1; 514/652

[56] References Cited

U.S. PATENT DOCUMENTS

| | | | |
|---|---|---|---|
| 3,951,821 | 4/1976 | Davidson | 252/1 |
| 4,474,986 | 10/1984 | Lietz | 564/349 |
| 4,945,114 | 7/1990 | Franke | 514/652 |
| 4,954,347 | 9/1990 | Kristen et al. | 424/456 |

Primary Examiner—Thurman K. Page
Assistant Examiner—William E. Benston, Jr.
Attorney, Agent, or Firm—Oblon, Spivak, McClelland, Maier & Neustadt, P.C.

[57] ABSTRACT

A cylindrical delayed release tablet with a convex or flat upper side and lower side is provided, along with a method for its production and a gelatin capsule containing 3–200 tablets of the same having identical or different release rates, wherein the tablet if made of β-phenylpropiophenone derivatives of the formula I as active ingredient

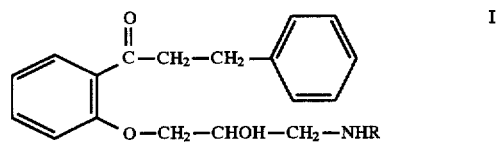

where R is n-propyl or 1,1-dimethylpropyl, and their pharmacologically acceptable salts, wherein the tablet has a height and diameter that are both, independently of one another, 1–3 mm, the active ingredient content is in the range from 81–99.9% of the weight of the microtablet, (but not taking into account the weight of any coating which is present, the active ingredient density is greater than 1, the release of active ingredient in the USP paddle method at 50 rpm is 80% as a maximum after 3 hours and as a minimum after 24 hours, the release rate is virtually independent of the pressure when compressing the tablets, and the tablet contains no release-delaying ancillary substance but can contain 0.1–5% by weight of a lubricant and 0–18.9% by weight of other conventional ancillary substances.

6 Claims, 11 Drawing Sheets

DELAYED RELEASE MICROTABLET OF β-PHENYLPROPIOPHENONE DERIVATIVES

This application is a 35USC371 of PCT/EP94/00949 filed Mar. 24, 1994.

BACKGROUND OF THE INVENTION

1. Field of the Invention

The present invention relates to cylindrical microtablets of β-phenylpropiophenone derivatives with a high content and density of active ingredient and a delayed release which is independent of the compressive force, with no release-delaying ancillary substances.

2. Discussion of the Background

Reference to β-phenylpropiophenone derivatives hereinbefore and hereinafter always includes and particularly means their physiologically acceptable salts, preferably the hydrochloride.

In the prior art the release of active ingredient from tablets is delayed either by a release-delaying matrix in which the active ingredient is embedded, or by a release-delaying coating through which the digestive fluid diffuses in and the active ingredient diffuses out.

Both principles have considerable disadvantages. For example, matrix tablets contain relatively large amounts of ancillary substances so that the volume of the tablet for a given dose of active ingredient is relatively large, which is unpleasant for the patient. On the other hand, film-coated tablets are elaborate to produce and, in particular, mechanically sensitive. The slightest damage to the lacquer film leads to the risk of sudden release of the entire content of active ingredient (dose dumping), which is extremely undesirable (local and temporal overdose with adverse side effects; short total action time).

Both matrix and film-coated delayed release tablets normally have diameters of about 6 to 12 mm or more and are therefore unable to pass through the closed pylorus. The release and absorption of their total content of active ingredient concentrated at one site in the gastrointestinal tract depends on the conditions prevailing at this site, which results in wide interindividual and intraindividual variation in the plasma level.

This variation is less with multiple unit delayed release forms because the units are distributed uniformly along the gastrointestinal tract and can also pass through the closed pylorus. Usually employed as multiple unit forms are pellets with a diffusion lacquer packed into hard gelatin capsules. It is possible to produce matrix pellets only with very low doses of medicinal substances because, owing to the large surface area, even more matrix substance would be required than for the bolus delayed d release tablet.

For example, the Patent Applications GB 2 176 999 and WO 92/04013 disclose small matrix delayed release tablets which likewise contain relatively large amounts of release-delaying ancillary substances. The Patent Application EP 22 17 32 claims delayed release tablets of active ingredients with low solubility, which contain 60–80% active ingredient in addition to at least four auxiliaries. The release from these bolus forms is, as described in the patent, highly dependent on the granulation process and the equipment used for manufacture.

It is furthermore generally known that an increase in the compressive force in tablet production is associated with a slowing of the release of active ingredient. This applies both to fast release tablets and to delayed release tablets (Patent Application WO 92/00064). Since the compressive forces fluctuate, despite the most up to date machine engineering, the resulting release rates vary. An additional factor is the variation between batches in the compression properties, which derives from the variability in the granules to be compressed. Differences in the particle size, porosity, surface structure, wettability etc. may have a large effect on the compression properties and the delaying of release.

SUMMARY OF THE INVENTION

It is an object of the present invention to overcome the disadvantages of the prior art, ie. to develop propafenone and diprafenone tablets with a small size, high content and density of active ingredient and release of active ingredient which is independent of the compressive force and uniform over a lengthy period.

We have found that this object is achieved by the microtablets of the present invention. This is because it has been found, surprisingly, that it is possible in the present case to produce delayed release tablets without release-delaying ancillary substances. This is all the more surprising because other medicinal substances with a water solubility similar to that of propafenone hydrochloride (0.7%), for example cimetidine hydrochloride or paracetamol, are 90% released in 1 hour from the same preparation.

DETAILED DESCRIPTION OF THE PREFERRED EMBODIMENTS

By comparison with other substances, propafenone HCl is extremely difficult to compress. A bolus tablet with commercial dosages of 150–300 mg and an active ingredient content above 80% cannot be produced under production conditions. By contrast, the microtablets according to the invention can, surprisingly, be produced at a relatively high machine speed without problems concerning friability and hardness, and specifically with active ingredient contents in the range from 81 to 99.9, preferably 85 to 99.5, % by weight and with an active ingredient density above 1. Such high contents of active ingredients of this type in tablets have not previously been reached.

The microtablets according to the invention are cylindrical with a flat or convex upper side and lower side and with a diameter and height which are preferably approximately equal and, independently of one another, from 1 to 3, preferably 1.5 to 2.5 mm.

Figure 11:
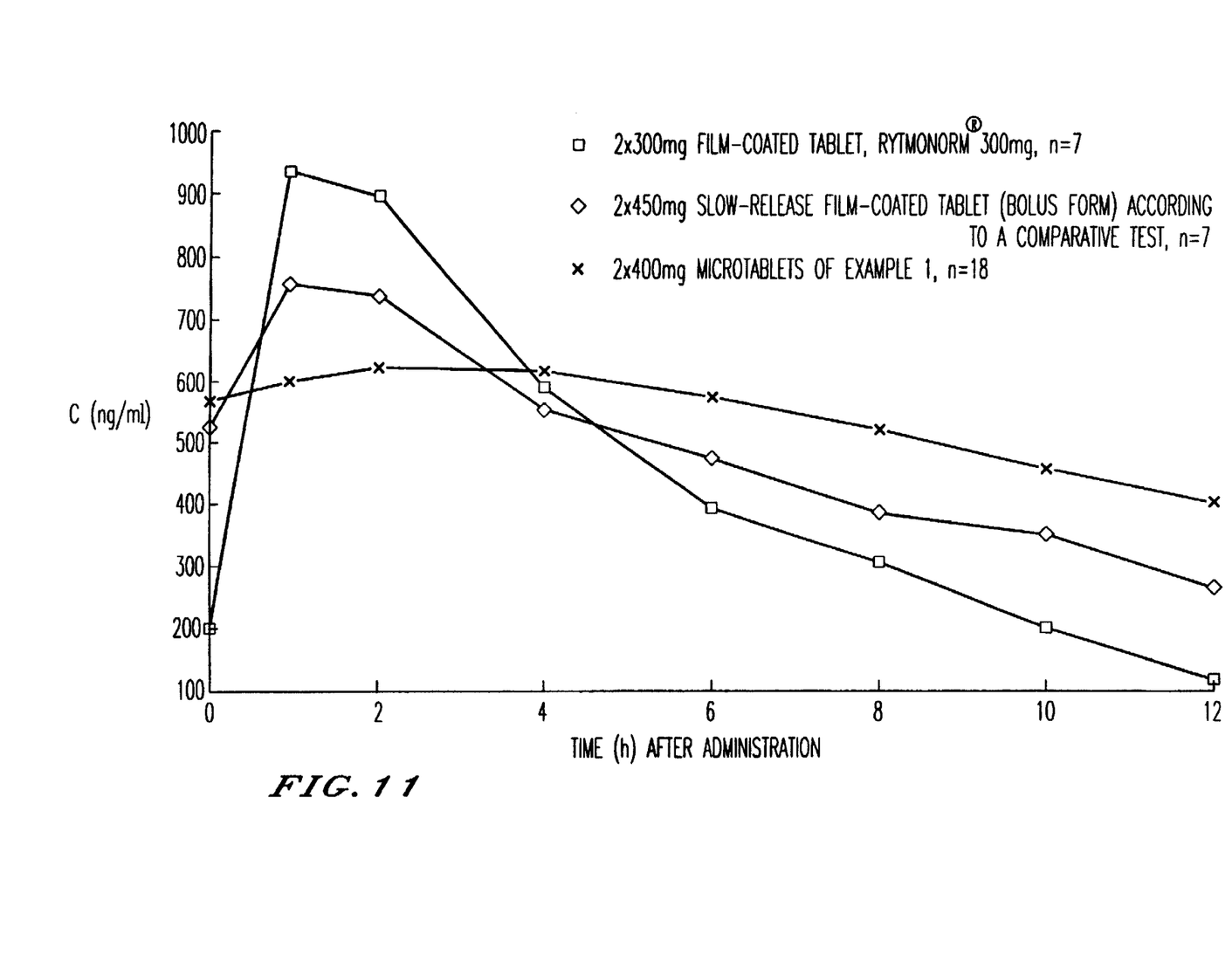

It was furthermore not predictable that the release of active ingredient is, in contrast to usual experience, virtually independent of the pressure when compressing the tablets and, moreover, over a wide range of pH of the medium. "Virtually independent" means that the effect can be neglected for practical purposes. This ensures release at a constant rate. It is adjusted via the size of the tablet and possibly by additives which increase the release rate so that the release of active ingredient after 3, preferably 5, hours is not more than 80 and after 24, preferably 15, hours is not less than 80%. Surprisingly, the microtablets according to the invention also display distinct advantages in vivo unlike conventional delayed release forms such as a bolus delayed release form with similar in vitro release. Despite the short half-life, a pronounced blood level plateau develops (FIG. 11). The fluctuations in the blood level are considerably less with the microtablets. This is evident from the $t_{75\%}$ (period in the dosage interval during which the plasma levels are at least 75% of the maximum level), which is 8 to 9 hours with the microtablets according to the invention compared with 5 to 6 hours with the bolus delayed release form, and from the PTF (peak to trough fluctuation; cf. H. P. Koch and W. A. Ritschel, Synopsis der Biopharmazie und Pharmakokinetik, Ecomed-Verlagsgesellschaft mbH, Landsberg und München, 1986)

$$PTF(\%) = \frac{C_{max} - C_{min}}{\frac{AUC}{\Delta t}} \times 100$$

for the AUC, cf. J. K. Aronson et al., Europ. J. of Clinical Pharmacology 35 (1988), 1–7.
which has a value for the microtablets which is only about half that for the bolus forms, in particular less than 75, preferably less than 60, %. The microtablets accordingly increase therapeutic safety because excessive peaks of plasma levels and the side effects caused thereby do not occur, the plasma level does not fall below the minimum effective level, and the bioavailability of this form is unaffected by food intake, in contrast to the bolus delayed release form.

The AUC found for the bolus delayed release form is 50% higher when fasting.

In general, the microtablets show smaller intra- and inter-individual differences by comparison with the bolus delayed release form.

The microtablets according to the invention furthermore have the advantage that when introduced into gastric or intestinal fluid they show no tendency to stick or adhere. This ensures that they pass as individual articles through the gastrointestinal tract and, moreover, do not become attached to the wall of the stomach or intestine and induce irritation. Sticking or adhesion properties of this type are displayed, for example, by small articles with hydrophilic release-delaying polymers (cf. WO 92/04013).

The production of delayed release forms with hydrophilic release-delaying polymers often requires the use of organic solvents during granulation so that swelling does not start even during this process. It is possible entirely to dispense with this in the production of the microtablets according to the invention.

Presentations with hydrophilic release-delaying polymers additionally have the disadvantage that, because of the tendency to sorption and swelling, they are sensitive to a change in humidity during storage. These formulations are damaged by high humidities in particular. The microtablets according to the invention are stable even at relatively high humidities because of the insensitivity of the materials used. Even after storage at 93% rel. humidity for 21 days the water uptake is less than 1%, and no visible change is detectable.

The microtablets according to the invention are produced in conventional pharmaceutical equipment by the following steps: granulation, drying, mixing, tabletting.

The particle size of the active ingredient is, within the conventional pharmaceutical range, of only minor or no importance in the production of the microtablets according to the invention, against all expectations. This means that it is possible to convert propafenone hydrochloride and diprafenone hydrochloride of different particle sizes into products of the same quality.

Granulation and drying are preferably carried out in a fluidized bed. However, the agglomeration can also be carried out in a horizontal or vertical mixer.

After the wet granules have been passed through a screen of suitable mesh width they are dried either in a circulating air dryer or in a fluidized bed. The particle size of the granules should be below 1 mm, preferably below 0.8 mm.

It is possible to employ all conventional binders or adhesives for the agglomeration, eg. polyvinylpyrrolidone, vinylpyrrolidone/vinyl acetate copolymers, gelatin, hydroxypropylmethylcellulose, hydroxypropylcellulose, polymers of methacrylic acid and its esters. It is possible to dispense with the use of a binder by using a solution of active ingredient as granulation liquid. Water without additives is preferred as granulation liquid.

After the granules have been dried to the defined water content, 0.1–5, preferably 0.3–2, % by weight of a lubricant for the tabletting are mixed in homogeneously. It is likewise possible to use for this purpose all conventional substances such as talc, magnesium stearate, calcium stearate, stearic acid, calcium behenate, glycerin palmitostearate, sodium acetate, polyethylene glycol, sodium stearate [sic] fumarate. In addition, up to 18.9% by weight of other conventional ancillary substances can be added, for example colorants, stabilizers, fillers, wetting agents, flow regulators but no release-delaying agents.

The tabletting takes place in a suitable tabletting machine equipped with multiple microtablet punches. The resulting microtablets have a cylindrical shape with flat or convex surface [sic]. The height and the diameter can be varied independently of one another. It is often expedient, to increase the apparent density and improve flowability, to match the height of the microtablets to the diameter.

Another element in the control of release besides the size of the microtablets is the addition of wetting agents which increase the rate of dissolution. Wetting agents which can be used are, on the one hand, surfactants such as polyoxyethylene fatty acid esters, polyoxyethylene fatty alcohol ethers, fatty acid salts, bile acid salts, alkyl sulfates or ethylene oxide/propylene oxide block copolymers or, on the other hand, genuinely water-soluble substances such as polyethylene glycols, urea, sodium chloride, sorbitol, mannitol, glycine, nicotinamide, or salts of citric acid, tartaric acid or phosphoric acid. In this case the rate of release increases in parallel with the rise in the wetting agent concentration.

The wetting agent can have been incorporated into the granules or else be subsequently mixed in together with the lubricant. This is, of course, possible only with solid wetting agents. The wetting agent concentration is 0.1–15, as a rule 1–10, % of the total mass.

To increase the rate of erosion of the active ingredient from the tablet surface, and thus the release of active ingredient, it is also possible to use disintegrants in concentrations of 0.001–0.5, preferably 0.01–0.1, %, which are far below the conventional concentrations.

As a rule, the microtablets can be packed into gelatin capsules directly using conventional filling machines. It may occasionally be advantageous for the microtablets, before the packing, to be provided with a readily soluble film coating which does not influence the release.

In addition, it is in many cases expedient to combine delayed release with instant release or not so delayed release microtablets. This results in release of an initial dose at once, followed by the slow release of the maintenance dose. Modern capsule filling machines are able to meter two products into one capsule without problems.

The instant release microtablet differs from the delayed release microtablet in that it contains conventional amounts of disintegrant, swelling agent, pore former, which bring about rapid disintegration of the microtablet into small fragments and rapid dissolution of the active ingredient.

The microtablets of the examples always had a diameter and height each of 2 mm, and the density of active ingredient was always more than 1.

EXAMPLES

Figure 1:
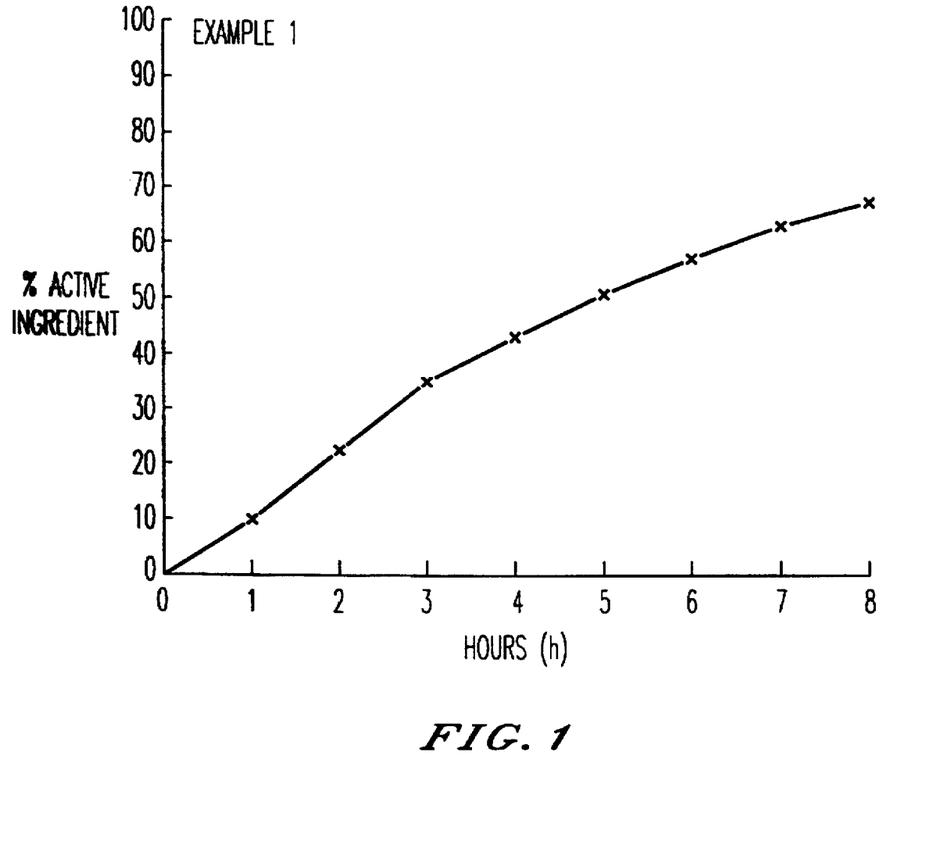

Example 1 (FIG. 1)

Propafenone delayed release microtablets

| Composition | |
|---|---|
| Propafenone HCl | 6.25 mg (96%) |
| Hydroxypropylmethylcellulose | 0.20 mg |
| Magnesium stearate | 0.05 mg |
| Total weight | 6.50 mg |

30kg of propafenone HCl were granulated with 10 kg of a 10% strength hydroxypropylmethylcellulose solution (Pharmacoat® 603) and dried in a fluidized bed granulator. The granules were passed through a screen of suitable mesh width and then mixed in a plowshare mixer with the stated amount of magnesium stearate.

The microtablets were produced in a rotary tabletting machine equipped with multiple microtablet punches.

The number of microtablets corresponding to the dose to be administered was packed into hard gelatin capsules using a suitable capsule filling machine.

TABLE 1

Results of studies on volunteers with propafenone HCl microtablets of Example 1 and a bolus delayed release form according to the comparative test (n = 18, dose: 400 mg of propafenone HCl, repeated administration)

| | | Microtablets | | Bolus delayed release form | |
|---|---|---|---|---|---|
| | | fasting | non-fasting | fasting | non-fasting |
| AUC | ng · h / ml | 5 500 | 5 500 | 6 900 | 4 700 |
| t₇₅% | (h) | 8–9 | 8–9 | 5–6 | 5–6 |
| PTF | (%) | 52 | 56 | 88 | 106 | n = number of volunteers
ng = nanogram
h = hours

Figure 2:
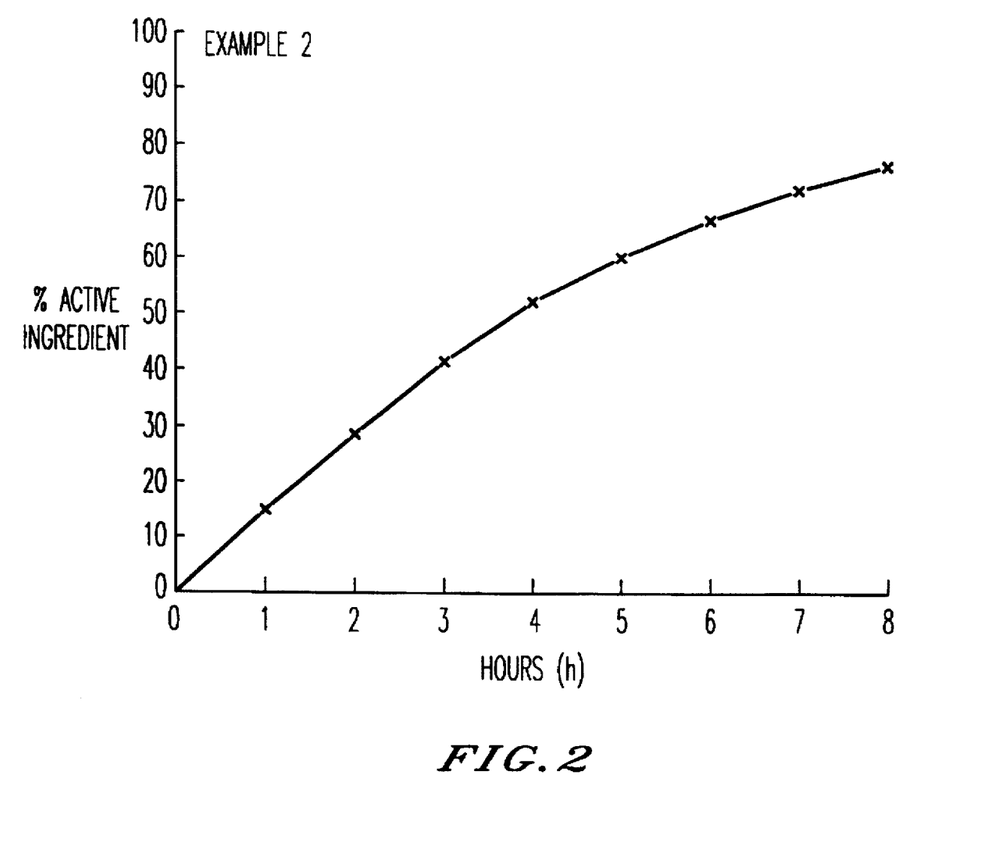

Example 2 (FIG. 2)

Propafenone delayed release microtablets

| Composition | |
|---|---|
| Propafenone HCl | 5.92 mg (91%) |
| Hydroxypropylmethylcellulose | 0.20 mg |
| Poloxamer 188 (USP) | 0.33 mg |
| Magnesium stearate | 0.05 mg |
| Total weight | 6.5 mg |

Production took place as in Example 1. The required amount of poloxamer 188 together with the magnesium stearate were mixed with the granules in a plowshare mixer.

Figure 3:
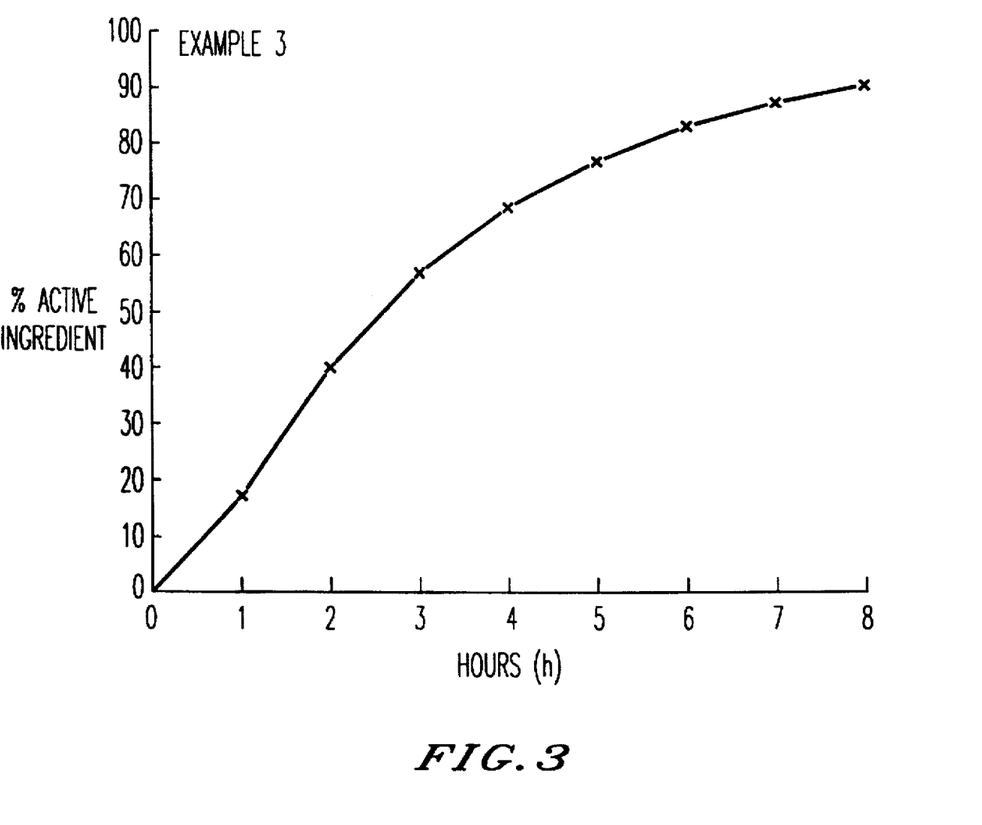

Example 3 (FIG. 3)

Propafenone delayed release microtablets

| Composition | |
|---|---|
| Propafenone HCl | 5.61 mg (86%) |
| Hydroxypropylmethylcellulose | 0.19 mg |
| Poloxamer 188 | 0.65 mg |
| Magnesium stearate | 0.05 mg |
| Total weight | 6.5 mg |

Production took place as in Example 2.

Figure 4:
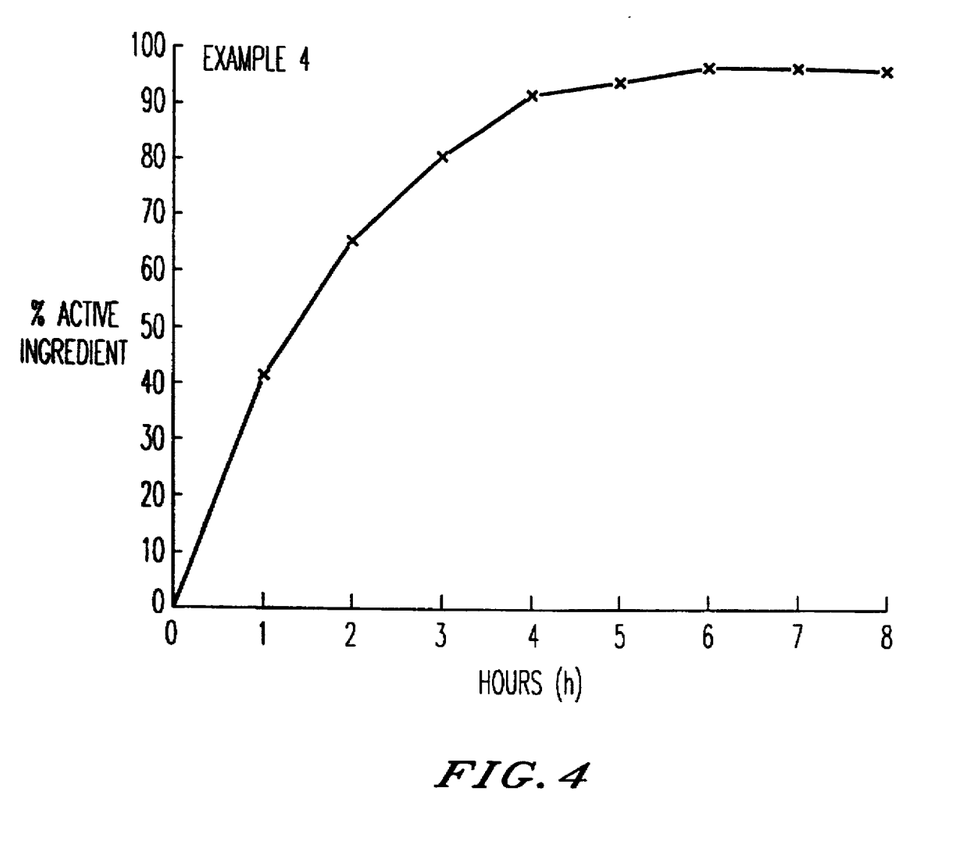

Example 4 (FIG. 4)

Propafenone delayed release microtablets

| Composition | |
|---|---|
| Propafenone HCl | 6.0 mg (86%) |
| Hydroxypropylmethylcellulose | 0.2 mg |
| Calcium hydrogen phosphate | 0.613 mg |
| Monoglyceride (Myvatox ®) | 0.15 mg |
| Crosslinked polyvinylpyrrolidone | 0.007 mg |
| Magnesium stearate | 0.03 mg |
| Total weight | 7.0 mg |

Production took place as in Example 2.

Figure 5:
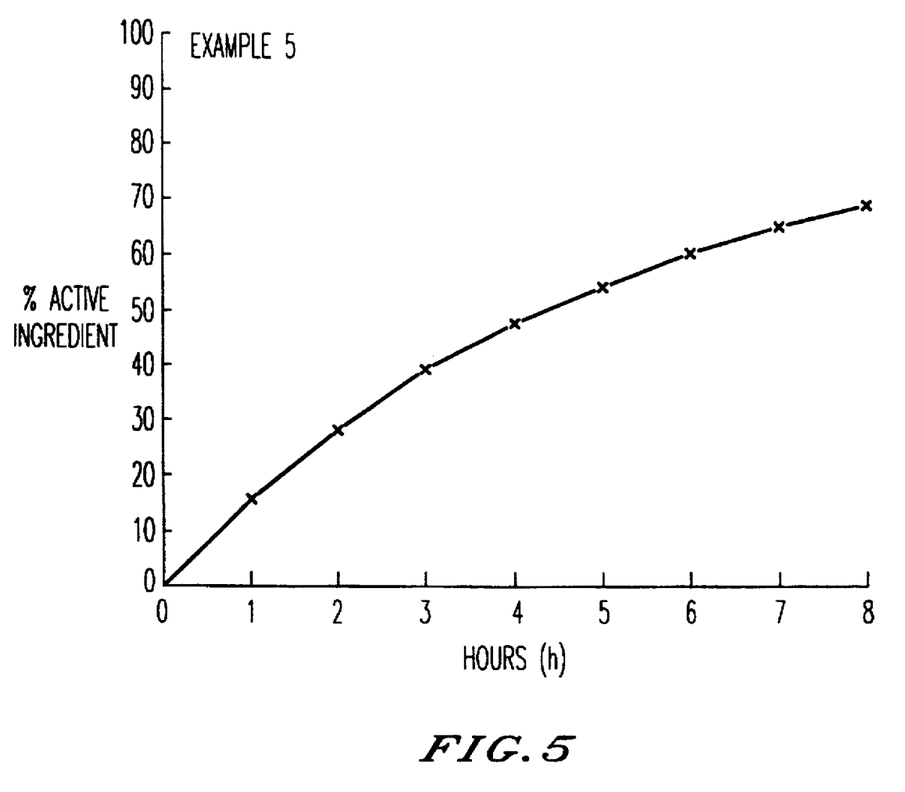

Example 5 (FIG. 5)

Propafenone delayed release microtablets

| Composition | |
|---|---|
| Propafenone HCl | 5.70 mg (81%) |
| Gelatin | 0.18 mg |
| Calcium hydrogen phosphate | 0.38 mg |
| NaCl | 0.70 mg |
| Magnesium stearate | 0.04 mg |
| Total weight | 7.0 mg |

Production took place as in Example 1. A 10% strength gelatin solution was used as granulating agent. The amount of NaCl was mixed in with the magnesium stearate.

Figure 6:
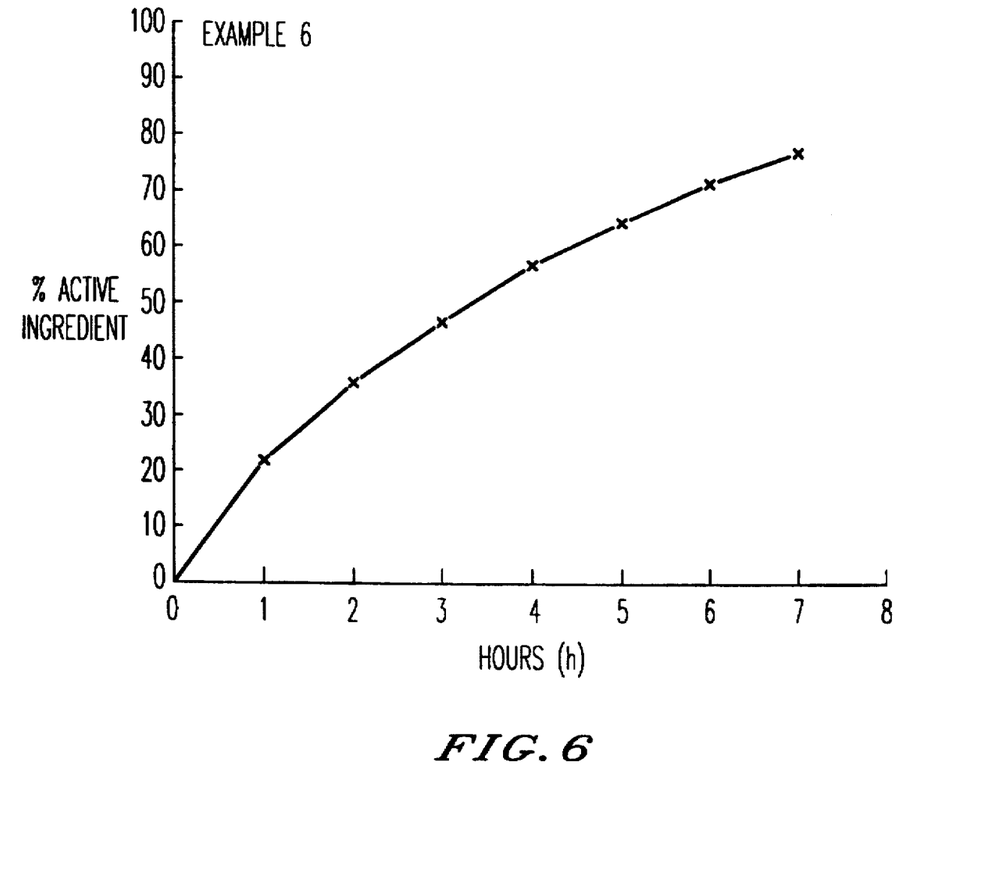

Example 6 (FIG. 6)

Propafenone delayed release microtablets

| Composition | |
|---|---|
| Propafenone HCl | 5.83 mg (83%) |
| Hydroxypropylmethylcellulose | 0.17 mg |
| β-Cyclodextrin | 0.9 mg |
| Magnesium stearate | 0.1 mg |
| Total weight | 7.0 mg |

Production took place as in Example 2.

Figure 7:
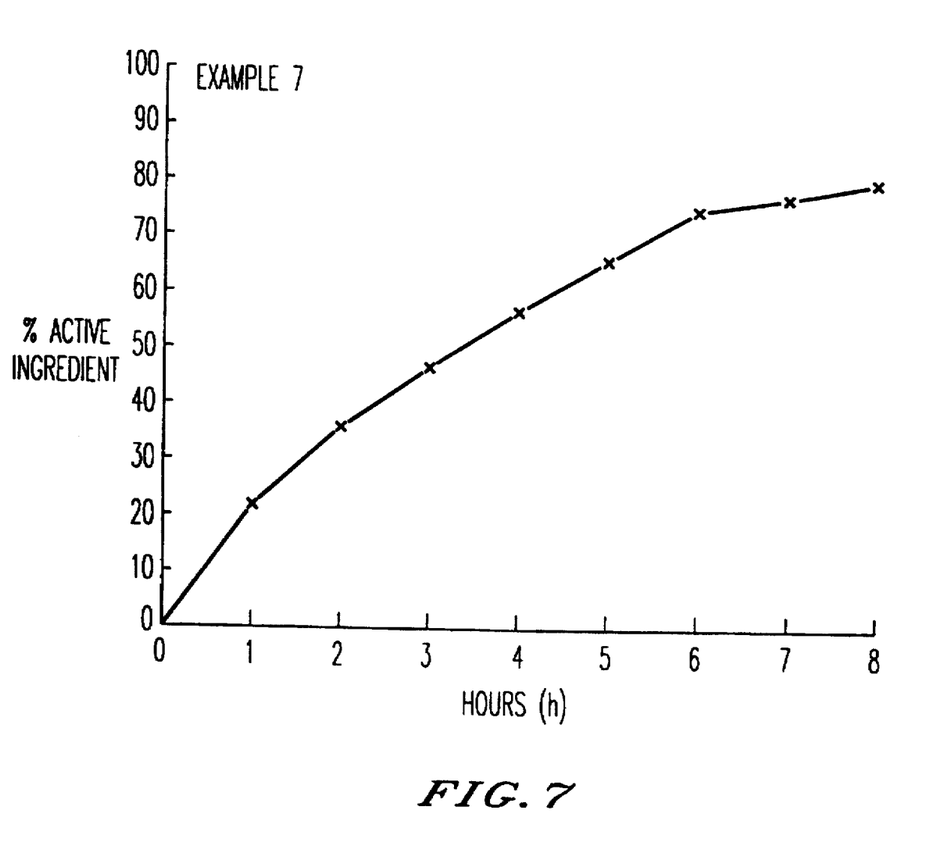

Example 7 (FIG. 7)

Gelatin capsules with propafenone delayed release microtablets and propafenone instant release microtablets To achieve a higher initial release, 14 instant release microtablets and 55 delayed release microtablets were packed into hard gelatin capsules in a suitable capsule filling machine.

| Composition of the instant release microtablets | |
|---|---|
| Propafenone HCl | 6.05 mg (93%) |
| Hydroxypropylmethylcellulose | 0.20 mg |
| Sodium carboxymethylstarch | 0.20 mg |
| Magnesium stearate | 0.05 mg |
| Total weight | 6.5 mg |

The instant release microtablets were produced as in Example 2.

The delayed release microtablets were produced as in Example 1.

Figure 8:
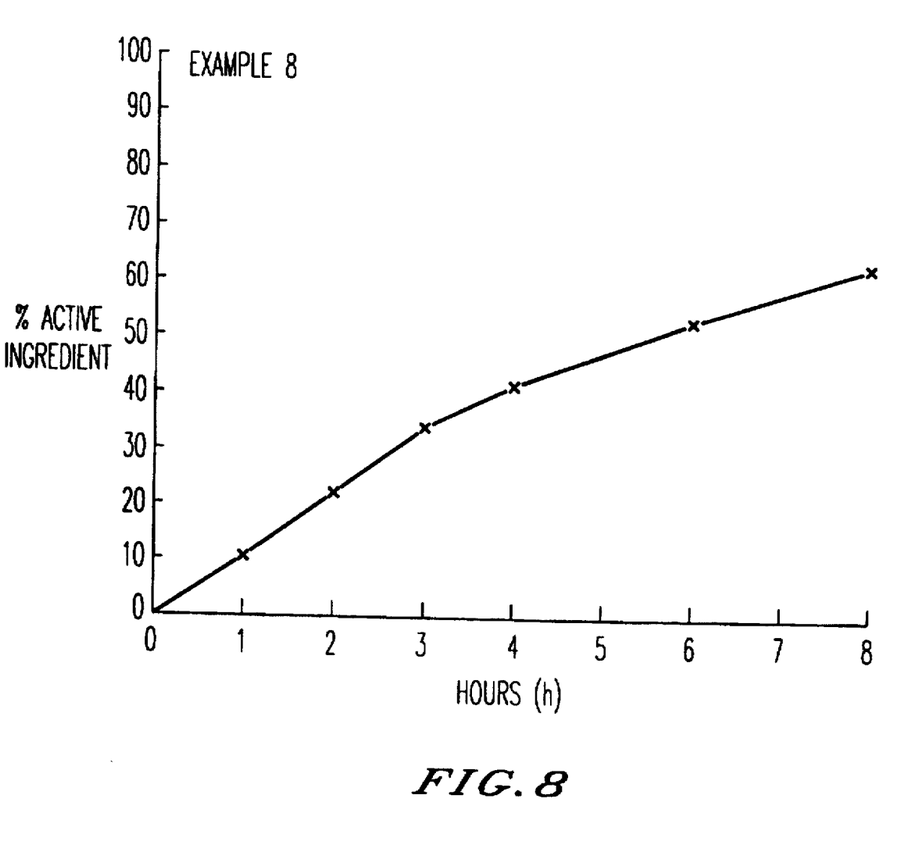
Figure 9:
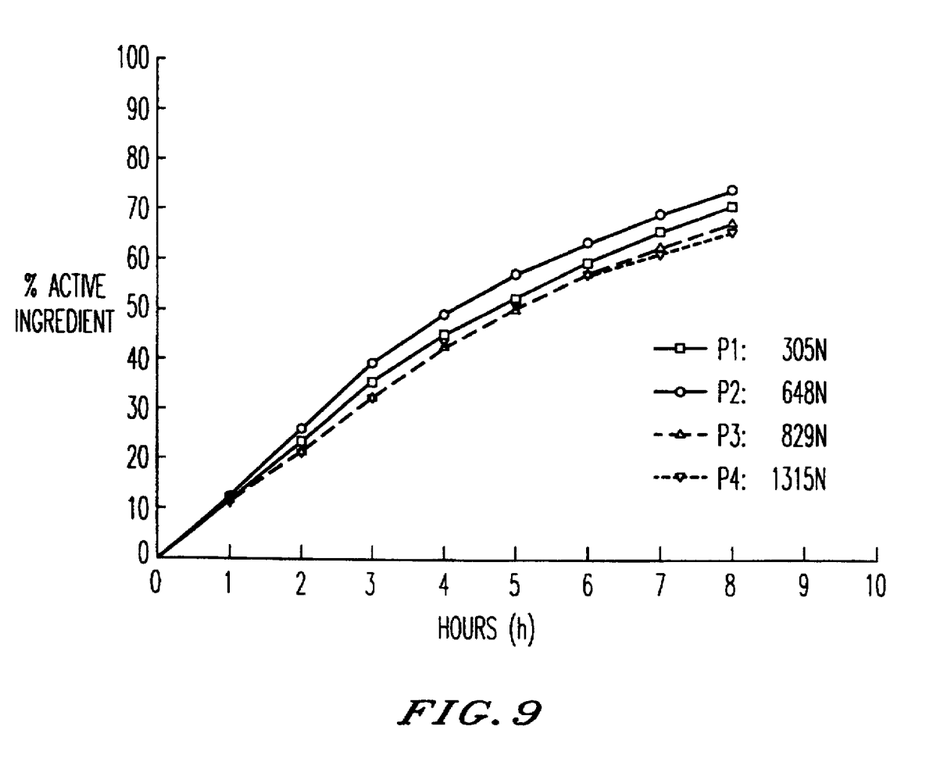
Figure 10:
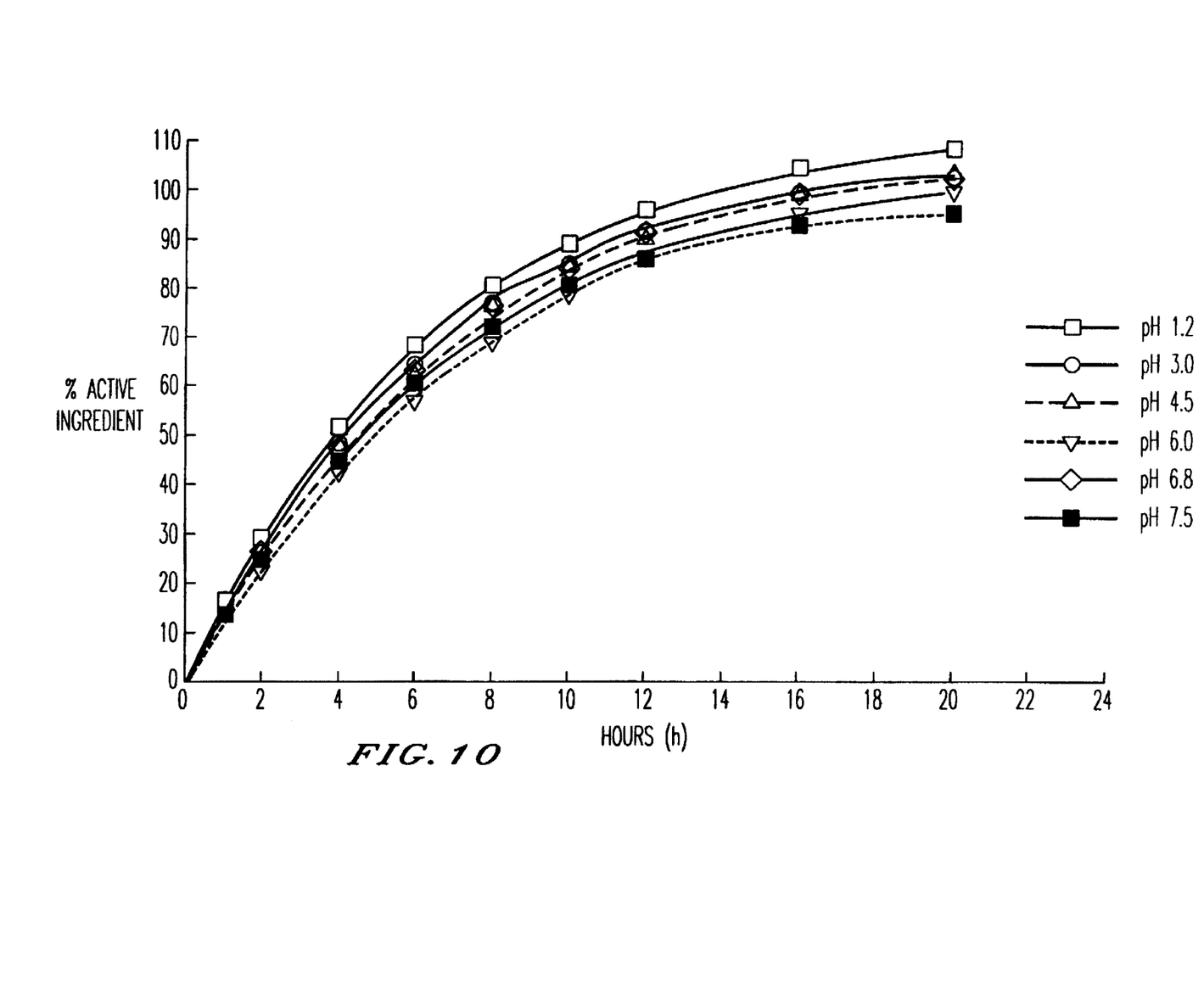

Example 8 (FIG. 8)

Propafenone delayed release microtablets

| Composition | |
|---|---|
| Propafenone HCl | 6.48 mg (99.7%) |
| Magnesium stearate | 0.02 mg |
| Total weight | 6.50 mg |

Propafenone hydrochloride and magnesium stearate were mixed in a plowshare mixer and subsequently compressed to microtablets.

The in vitro release plots (FIGS. 1 to 10) were determined using a USP paddle apparatus with 0.08 molar HCl in the first two hours and then phosphate buffer pH 6.8. The paddle rotated at 50 rpm.

Comparative test

Propafenone delayed release bolus film-coated tablet

| Composition | |
|---|---|
| Propafenone HCl | 450.0 mg |
| Sodium alginate | 112.0 mg |
| Microcrystalline cellulose type PH 101 | 37.0 mg |
| Copolymers of acrylic and methacrylic esters with a small content of quaternary ammonium groups (Eudragit® RS) | 15.0 mg |
| Gelatin | 55.0 mg |
| Magnesium stearate | 3.5 mg |
| Microcrystalline cellulose type PH 102 | 12.5 mg |
| Readily soluble film coating | 15.0 mg |
| Total weight | 700.0 mg |

Propafenone hydrochloride, sodium alginate, microcrystalline cellulose (type PH 101) and Eudragit RS were mixed in a vertical mixer and granulated with 20% strength gelatin solution. The wet granules were dried in a fluidized bed dryer with inlet air at 60° C. After passing through a screen of suitable mesh width, magnesium stearate and microcrystalline cellulose (type PH 102) were admixed in a horizontal mixer and subsequently the mixture was compressed to oblong tablets (dimensions 18×8.7 mm) in a rotary tabletting machine. The readily soluble coating was applied in a horizontal coater.

Determination of in vitro release in a paddle apparatus at 50 rpm produced the following results (in %):

| 1st hour | 3.8 |
|---|---|
| 2nd hour | 5.5 |
| 3rd hour | 23.7 |
| 4th hour | 43.0 |
| 6th hour | 75.4 |
| 8th hour | 89.5 |

The in vitro release from the delayed release bolus film-coated tablet is thus similar to that of the delayed release microtablets according to the invention. Nevertheless, the in vivo release is entirely different and, in fact, better according to the invention, cf. drug levels shown in FIG. 11.

We claim:

1. A cylindrical delayed release microtablet with a convex or flat upper side and lower side of β-phenylpropiophenone derivatives of the formula I as active ingredient where R is n-propyl or 1,1-dimethylpropyl, and their pharmacologically acceptable salts, wherein a) the height and diameter are, independently of one another, 1–3 mm, b) the active ingredient content is in the range from 81 to 99.9% of the weight of the microtablet, c) the active ingredient density is greater than 1, d) the release of active ingredient in the USP paddle method at 50 rpm is 80% as a maximum after 3 hours and as a minimum after 24 hours, e) the release rate is virtually independent of the pressure when compressing the tablets, and f) the tablet contains no release-delaying ancillary substance but 0.1–5% by weight of a lubricant and 0–18.9% by weight of other conventional ancillary substances.

2. A tablet as claimed in claim 1, which in vivo results in a pronounced plasma level plateau with a PTF<75% and whose bioavailability does not depend on the intake of food.

3. A tablet as claimed in claim 1, wherein the active ingredient is propafenone hydrochloride.

4. A tablet as claimed in claim 1, wherein the height and diameter are approximately the same.

5. A gelatin capsule which contains 3–200 tablets as claimed in claim 1 with identical or different release rates.

6. A process for producing cylindrical delayed release microtablets as claimed in claim 1, which comprises a homogeneous mixture of 81–99.9% by weight of the granulated active ingredient with a particle size below 1 mm, 0.1–5% by weight of a lubricant and 0–18.9% by weight of other conventional ancillary substances which do not delay release being compressed in a cylindrical mold with a height and diameter each of 1–3 mm and being removed from the mold.

* * * * *

UNITED STATES PATENT AND TRADEMARK OFFICE
CERTIFICATE OF CORRECTION

PATENT NO. : 5,681,588
DATED : October 28, 1997
INVENTOR(S) : Karl KOLTER et al.

It is certified that error appears in the above-identified patent and that said Letters Patent is hereby corrected as shown below:

On the title page, Item [87], the PCT Pub. Date should read:

-- Oct. 13, 1994 --

Signed and Sealed this

Tenth Day of February, 1998

Attest:

BRUCE LEHMAN

*Attesting Officer*    *Commissioner of Patents and Trademarks*